United States Patent
Young et al.

[11] 4,221,791
[45] Sep. 9, 1980

[54] SUBSTITUTED QUINOXALINE DIOXIDES

[75] Inventors: Vernon V. Young; Robert D. Williams; Richard E. Ivy, all of Terre Haute, Ind.

[73] Assignee: International Minerals & Chemical Corp., Terre Haute, Ind.

[21] Appl. No.: 40,835

[22] Filed: May 21, 1979

[51] Int. Cl.³ .................. A61K 31/495; C07D 241/52
[52] U.S. Cl. ........................... 424/248.4; 424/250; 424/251; 426/532; 542/420; 542/422; 544/116; 544/295; 544/353
[58] Field of Search .................. 544/353, 116, 295; 424/250, 251, 248.4; 542/420, 422; 426/532

[56] References Cited

U.S. PATENT DOCUMENTS

| | | | |
|---|---|---|---|
| 3,644,363 | 2/1972 | Kim | 544/353 |
| 3,926,992 | 12/1975 | McFarland | 544/353 |
| 4,100,284 | 7/1978 | Cue | 544/353 |

Primary Examiner—Paul M. Coughlan, Jr.
Attorney, Agent, or Firm—Robert H. Dewey

[57] ABSTRACT

Compounds represented by the formula:

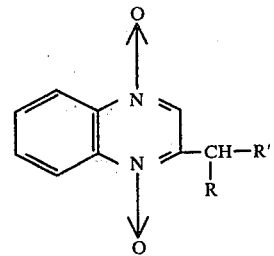

where R and R' collectively are (a) $=NOCH_2COOCH_3$,

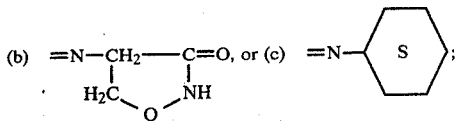

or R is hydroxyl or alkoxy and R' is

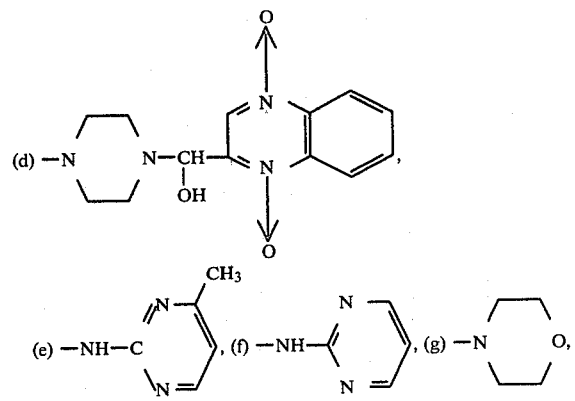

(h) —NHOH, or (i) —NHNHCO₂CH₃. The compounds promote the growth rate of animals and improve the feed efficiency.

16 Claims, No Drawings

SUBSTITUTED QUINOXALINE DIOXIDES

BACKGROUND OF THE INVENTION

This invention relates to substituted quinoxaline dioxides. In a particular aspect this invention relates to a method of promoting the growth of animals.

In the business of raising animals for food, it is essential to feed the animals those rations and adjuncts thereto, such as growth promoter stimulants, that provide a rapid weight gain and a high conversion of feed to animal weight. Such compounds cause the animal to gain weight faster during the growth period, thus shortening the time required to bring the animal to market weight. A growth stimulant is a compound which elicits a response of an animal toward its optimum genetic potential from a depression in growth rate and feed efficiency caused by intestinal bacterial flora, stress and subclinical diseases. Some compounds also act to improve feed efficiency, i.e. they permit the animal to gain more weight per unit weight of food than would occur without the compound. Such compounds are highly advantageous in raising animals for food. Antibiotics such as penicillin, bacitracin and tetracyclines have been widely used for this purpose. Antibiotics have several disadvantages, however. There is the possibility that resistant strains of pathogenic organisms may develop. Also, these antibiotics are expensive to produce. Accordingly, there is a need for other agents to stimulate the growth of animals.

SUMMARY OF THE INVENTION

It is an object of this invention to provide substituted quinoxaline dioxides.

It is another object of this invention to provide a method for promoting the growth of animals.

It is yet another object of this invention to provide a method for improving the feed efficiency of animals.

Still other objects of this invention will be apparent to those skilled in the art from the disclosure herein.

It is the discovery of this invention to provide compounds represented by the formula

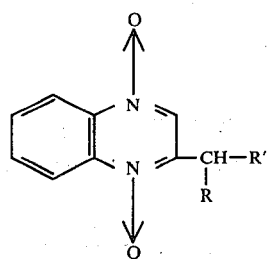

where R and R' collectively are (a)=NOCH$_2$COOCH$_3$,

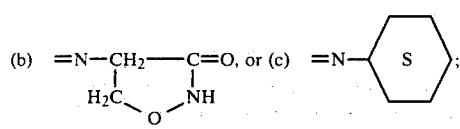

or R is hydroxyl or alkoxy and R' is

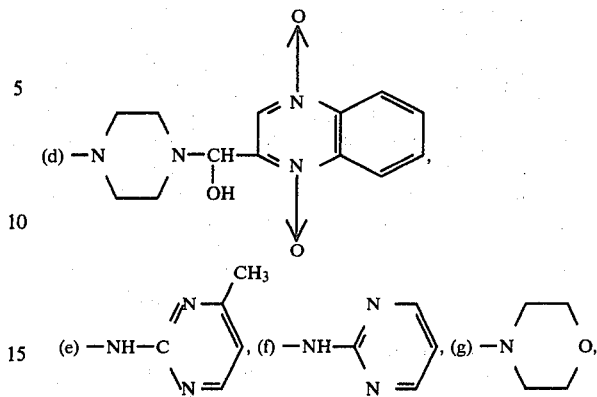

(h)—NHOH, or (i)—NHNHCO$_2$CH$_3$. The compounds promote the growth rate of animals and improve the feed efficiency and method of preparation. It is also an embodiment of this invention to provide a method of improving the growth rate of animals and increasing the feed efficiency.

DETAILED DISCUSSION

The compounds of this invention are readily prepared by reacting 2-formylquinoxaline-1,4-dioxide hydrate with a suitable compound, Compound A, for providing the values of R and R', viz: when R is hydroxyl, compounds A include piperazine; 2-aminopyrimidine; 2-amino-4-methylpyrimidine; morpholine; hydroxylamine (as the hydrochloride salt); and methyl carbazate. When R is alkoxy, compounds A include 2-aminopyrimidine and 2-amino-4-methylpyrimidine. When R and R' are collectively (b) and (c) respectively, compounds A include cycloserine and cyclohexylamine. When R and R' are collectively (a), the compound is obtained by reacting 2-formylquinoxaline-1,4-dioxide oxime, a known compound, with methylbromoacetate.

The reaction proceeds readily, especially at elevated temperatures of 60°–80° C. and under alkaline conditions. Advantageously, water or a lower alkyl alcohol, e.g. of from 1 to 4 carbon atoms, preferably methanol, is used as a solvent. When a solvent is used, the formyl quinoxaline and alkaline agent are preferably heated to reflux temperatures, then the reagent of Compounds A is added with agitation and the heat source is removed. Agitation is continued until the mixture reaches room temperature, during which time a precipitate forms. It can be recovered by evaporating the alkyl alcohol, or alternatively it can be separated from the mother liquor, e.g. by filtration, centrifugation or decantation, and preferably rinsed with a small amount of alkanol solvent, e.g. methanol. When preferred, the product can be recrystallized.

The formyl quinoxaline dioxide hydrate used in the practice of this invention can be prepared by the acid hydrolysis of 2-formylquinoxaline-1,4-dioxide dimethyl acetal, which is a known compound, described by M. J. Haddadin et al., British Pat. No. 1,305,138. The hydrate compound is readily obtained by dissolving the dimethyl acetal compound in hot dilute hydrochloric acid (3.5–4.0%). The solution is allowed to cool and is then chilled whereupon the hydrate crystallizes. For a higher purity product, it may be desirable to treat the hot solution with activated charcoal and filtering before crystallization begins.

The alkaline conditions used in the production of the compounds of this invention can be provided by any suitable alkalinizing agent including sodium and potassium hydroxides or alkoxides and alkylamines, but generally strong amines such as tertiary alkylamines, e.g. triethylamine or tributylamine, are preferred. Also, the alkaline conditions can be provided by an excess of Compound A reagent. Generally from 0.1% to about 1.0% of the alkalinizing agent is sufficient.

It is an embodiment of this invention to provide a method for promoting the growth of animals and improving their feed efficiency by administering to them a compound of this invention.

It is contemplated that the method of this invention will be particularly suitable for animals raised for food such as fowl, ruminants, swine and rabbits. Although all members of the fowl family—i.e. chickens, turkeys, geese, ducks, guinea, pheasant and quail—will show increased rate of growth and improved feed efficiency, the method is particularly valuable for chicken broilers and turkeys. Of the ruminants, e.g. cattle, sheep and goats, the method is particularly of value for cattle, e.g. steers.

The method of administration of a compond of this invention is to incorporate it in the feed rations intended for the animal at a concentration of about 50–150 g/ton of feed, preferably about 100 g/ton. The animals are permitted to feed at liberty throughout the growth period. There are many specialized feed rations for different species of animals. The compounds of this invention can be used with any of the known rations.

The term "feed rations" is intended to mean the food provided for the animals, and it is not intended that the invention be limited thereby. Preferably the compound is thoroughly mixed with the feed ration so that it is uniformly dispersed throughout. However, it is also contemplated that it could be sprinkled on the daily food supplies in the form of a powder or as pellets. Thus, it is not intended that the invention be limited to any particular mode of administration.

Any of the known feed rations can be used in the practice of this invention and it is not intended that the invention be limited by the formulation of the ration. Feed rations are formulated to provide the animal for which it is intended with the essential nutrients, minerals, vitamins, bulk, etc. Formulation of these rations are well within the skill of nutritionists.

The invention will be better understood with reference to the following examples. It is understood, however, that these examples are intended only to illustrate the invention and it is not intended that the invention be limited thereby.

EXAMPLE 1

2-Formylquinoxaline-1,4-dioxide oxime, a compound known from U.S. Pat. No. 3,331,090 (2.0 g) was dissolved in 25 ml of methanol containing 0.25 g of sodium with stirring. The solution was heated and methyl bromoacetate, 1.5 g, was added. The heat source was removed and the solution was allowed to cool to room temperature with stirring. The precipitate which formed was isolated, rinsed with methanol and dried. There was obtained 2-quinoxalinylmethyleneaminoxyacetic acid methyl ester-1,4-dioxide, m.p. 185°–187° C. It was designated P-2227 for convenience and it analyzed as follows:

|  | C | H | N |
|---|---|---|---|
| Calc., %: | 51.99 | 3.61 | 15.16 |
| Found, %: | 52.74 | 3.88 | 15.04 |

The nuclear magnetic resonance spectrum agreed with proposed structure.

Growth promotion and improved feed efficiency were determined as follows:

Two groups of male two-day-old broiler-type chicks were placed into Petersime starter batteries and given feed and water ad libitum for the duration of each test. Each group was subdivided into six sub-groups with ten birds in each sub-group, thus providing sixty birds per group. One group received the basal feed ration, as given in the table and served as a control. The other group received the same ration, but in addition there was included P-2227 at a concentration of 100 g/ton. The basal ration was a rye diet which alters the microflora of the gut in the bird which results in a growth depressant effect. When a growth stimulant or promotant is added to the diet, the effect on the birds performance will be more apparent than if a corn base diet was used.

The test period was thirteen days. Individual live body weights and pen feed efficiencies were taken at 2 and 14 days of age. The data are given below. Growth promotion by P-2227 is indicated by the average percentage increase in weight over that of the control group, and feed efficiency is taken as the ratio of weight of feed consumed to weight gained and the increase of this ratio over the ratio exhibited by controls is taken as the increase of feed efficiency.

| Basal Ration | |
|---|---|
| Ground rye | 55.0 |
| Soybean meal 44% | 29.0 |
| Fish solubles 40% | 2.0 |
| Meat and bone meal 50% | 5.0 |
| Dehydrated alfalfa meal | 1.2 |
| Dried whey | 1.0 |
| Fat | 4.0 |
| Dicalcium phosphate 24% ca 18.5%° | 1.0 |
| Livestock mineral 24% ca 6%P | .75 |
| Salt | .50 |
| Vitamin and trace mineral premix | .50 |
| | 100 lbs |
| Analysis | |
| Protein | 23.3% |
| Calcium | 1.03% |
| Phosphorus | 0.84% |
| M.E. kg Calories/lb | 1260 |

The results obtained in the growth test are as follows:

|  | P-2227 | Control |
|---|---|---|
| Average wt gain per pen, g | 221.66 | 208.73 |
| Increased wt gain over control, % | 6.2 | — |
| Feed efficiency | 1.46 | 1.49 |
| Increased feed efficiency, % | 2.0 | — |

EXAMPLE 2

2-Formylquinoxaline-1,4-dioxide hydrate, 2.0 g, was dissolved in 80 ml of warm water, stirred and 1.0 g of cycloserine dissolved in 10 ml of water were added. The heat source was removed and the stirring was continued until the mixture was at room temperature. The precipitate which formed was isolated and dried. It was recrystallized from a mixture of dimethyl sulfoxide and isopropyl alcohol, 1 g/10 cc/20 cc. There was obtained the cycloserine adduct, designated P-2233 for convenience, wherein R and R' of the general formula are believed to be the moiety

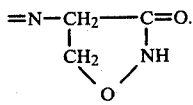

The compound, which decomposed on heating, analyzed as follows:

|  | C | H | N |
|---|---|---|---|
| Calc., %: | 52.55 | 3.68 | 20.43 |
| Found, %: | 52.16 | 4.16 | 15.69 |

The growth test of Example 1 was repeated in all essential details. The results were as follows:

|  | P-2233 | Control |
|---|---|---|
| Average wt gain per pen, g | 199.8 | 165.9 |
| Increased wt gain over control, % | 20.6 | — |
| Feed efficiency | 1.48 | 1.57 |
| Increased feed efficiency, % | 5.7 | — |

EXAMPLE 3

2-Formylquinoxaline-1,4-dioxide hydrate, 2.0 g, was dissolved in 25 ml of warm methanol containing four drops of triethylamine. While stirring, 0.5 g of cyclohexylamine in 10 ml of methanol was added at once. A precipitate formed immediately. The mixture was allowed to cool to room temperature with stirring. The precipitate was isolated and dried; there was obtained a Schiff's base wherein R and R' are collectively

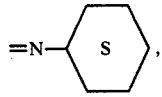

m.p. 142°–144° C. It was designated P-2251 for convenience. It analyzed as follows:

|  | C | H | N |
|---|---|---|---|
| Calc., %: | 66.40 | 6.32 | 15.49 |
| Found, %: | 66.39 | 6.45 | 14.87 |

The growth test of Example 1 was repeated in all essential details. The results are as follows:

|  | P-2251 | Control |
|---|---|---|
| Average wt gain per pen, g | 151.16 | 127.63 |
| Increased wt gain over control, % | 18.4 | — |
| Feed efficiency | 1.74 | 1.74 |
| Increased feed efficiency, % | 0.0 | 0 |

EXAMPLE 4

The experiment of Example 3 was repeated in all essential details except that piperazine was substituted for cyclohexylamine. There was obtained α,α-bis(2-quinoxazolinyl)-1,4-piperazinedimethanol-1,1',4,4'-tetraoxide, m.p. 170°–175° C. It was designated P-2256 for convenience and analyzed as follows:

|  | C | H | N |
|---|---|---|---|
| Calc., %: | 56.65 | 4.75 | 18.02 |
| Found, %: | 56.60 | 4.83 | 18.57 |

It was treated for growth promotion as described in Example 1. The following results were obtained:

|  | P-2256 | Control |
|---|---|---|
| Average wt gain per pen, g | 179.3 | 150.4 |
| Increased wt gain over control, % | 19.2 | — |
| Feed efficiency | 1.57 | 1.73 |
| Increased feed efficiency, % | 9.2 | — |

EXAMPLE 5

The experiment of Example 4 was repeated in all essential details except that 2-amino-4-methylpyrimidine was substituted for piperazine. There was obtained α-ethoxy-N-(4-methyl-2-pyrimidinyl)-2-quinoxalinemethanamine-1,4-dioxide, m.p. 102°–104° C. It was designated P-2245 for convenience. It analyzed as follows:

|  | C | H | N |
|---|---|---|---|
| Calc., %: | 55.64 | 5.55 | 20.28 |
| Found, %: | 55.49 | 5.43 | 20.14 |

The nmr spectrum was consistent with the proposed structure. The growth test results were as follows:

|  | P-2245 | Control |
|---|---|---|
| Average wt gain per pen, g | 227.32 | 217.25 |
| Increased wt gain over control, % | 4.6 | — |
| Feed efficiency | 1.47 | 1.55 |
| Increased feed efficiency, % | 5.2 | — |

EXAMPLE 6

The experiment of Example 4 was repeated in all essential details except that 2-aminopyrimidine was substituted for piperazine. There was obtained α-ethoxy-N-(2-pyrimidinyl)-2-quinoxalinemethanamine-1,4-dioxide, m.p. 192°–195° C. It was designated P-2247 for convenience.

The results of the growth test are as follows:

|  | P-2247 | Control |
|---|---|---|
| Average wt gain per pen, g | 184.8 | 134.8 |
| Increased wt gain over control, % | 37.1 | — |
| Feed efficiency | 1.58 | 1.73 |
| Increased feed efficiency, % | 8.7 | 0 |

EXAMPLE 7

The experiment of Example 4 was repeated in all essential details except that morpholine was substituted for piperazine. There was obtained 2-(N-hydroxymethylmorpholinyl)quinoxaline-1,4-dioxide, m.p.

155°–157° C. It was designated P-2250 for convenience. It analyzed as follows:

|  | C | H | N |
|---|---|---|---|
| Calc., %: | 56.31 | 5.45 | 15.16 |
| Found, %: | 56.92 | 5.40 | 14.81 |

The results of the growth promotion test were as follows:

|  | P-2250 | Control |
|---|---|---|
| Average wt gain per pen, g | 145.1 | 132.6 |
| Increased wt gain over control, % | 9.4 | — |
| Feed efficiency | 1.63 | 1.78 |
| Increased feed efficiency, % | 8.4 | — |

EXAMPLE 8

The experiment of Example 4 was repeated in all essential details except that 2-aminopyrimidine was substituted for piperazine and water was used as the solvent. There was obtained α-hydroxy-N-(2-pyrimidinyl)-2-quinoxalinemethanamine-1,4-dioxide, m.p. 189°–190° C. with decomposition. It was designated P-2252 for convenience. It analyzed as follows:

|  | C | H | N |
|---|---|---|---|
| Calc., %: | 54.73 | 3.89 | 24.55 |
| Found, %: | 55.11 | 4.05 | 24.20 |

The results of the growth promotion test are as follows:

|  | P-2252 | Control |
|---|---|---|
| Average wt gain per pen, g | 138.20 | 127.63 |
| Increased wt gain over control, % | 8.3 | — |
| Feed efficiency | 1.73 | 1.74 |
| Increased feed efficiency, % | 0.6 | 0 |

EXAMPLE 9

The experiment of Example 4 was repeated in all essential details except that hydroxylamine hydrochloride was substituted for piperazine. There was obtained α-(hydroxyamino)-2-quinoxalinemethanol-1,4-dioxide, m.p. 241°–243° C. with decomposition. It was designated P-2260 for convenience. It analyzed as follows:

|  | C | H | N |
|---|---|---|---|
| Calc., %: | 48.43 | 4.06 | 18.83 |
| Found, %: | 47.98 | 4.15 | 18.28 |

The nmr spectrum was consistent with the proposed structure. The results of the growth promotion test are as follows:

|  | P-2260 | P-2261 | Control |
|---|---|---|---|
| Average wt gain per pen, g | 188.4 | 196.2 | 130.9 |
| Increased wt gain, % | 43.9 | 49.9 | — |
| Feed efficiency | 1.56 | 1.55 | 1.73 |
| Increased feed efficiency, % | 9.8 | 10.4 | — |

EXAMPLE 10

The experiment of Example 4 was repeated in all essential details except that methyl carbazate was substituted for piperazine. There was obtained 2-(α-hydroxy-2-quinoxalinylmethyl)hydrazinecarboxylic acid methyl ester N', N⁴-dioxide, m.p. 242°–244° C. with decomposition. It was designated P-2261 for convenience and analyzed as follows:

|  | C | H | N | O |
|---|---|---|---|---|
| Calc., %: | 47.14 | 4.32 | 19.99 | 28.55 |
| Found, %: | 47.56 | 4.44 | 19.75 | 28.43 |

The nmr spectrum was consistent with the proposed structure.

The results of the growth test are given above.

We claim:

1. A compound represented by the formula

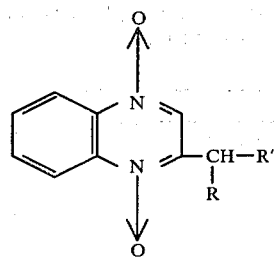

where R and R' collectively are (a)=NOCH$_2$COOCH$_3$,

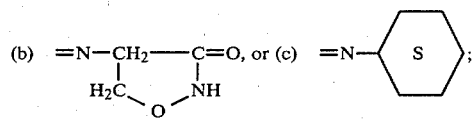

or R is hydroxyl or ethoxy and R' is

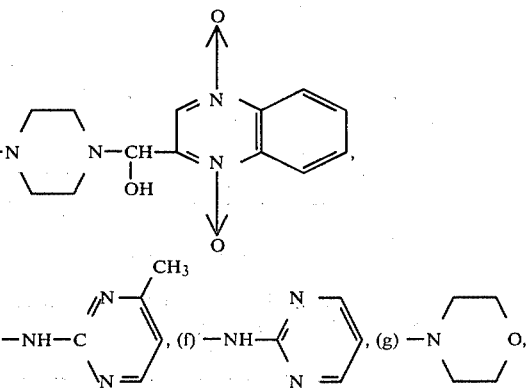

(h)—NHOH, or (i)—NHNHCO$_2$CH$_3$.

2. A compound of claim 1 wherein R is ethoxy.
3. A compound of claim 2 wherein R' is (e).
4. A compound of claim 2 wherein R' is (f).
5. A compound of claim 1 wherein R is hydroxy.
6. A compound of claim 5 wherein R' is (g).
7. A compound of claim 5 wherein R' is (f).
8. A compound of claim 5 wherein R' is (h).

9. A compound of claim 5 wherein R' is (i).

10. A compound of claim 1 wherein R and R' collectively are represented by (a).

11. A compound of claim 1 wherein R and R' are collectively represented by (b).

12. A compound of claim 1 wherein R and R' are collectively represented by (c).

13. A method of increasing the growth rate of animals comprising orally administering to the animal a compound of claim 1.

14. The method of claim 13 wherein the compound is administered in the animal's feed and is present in an amount of from 50–150 g per ton of feed.

15. An animal feed consisting essentially of a nutrient feed ration and a compound of claim 1 in an amount effective to promote the growth of animals.

16. The feed ration of claim 15 wherein said compound is present in an amount of from 50 to 150 g per ton of feed.

* * * * *

UNITED STATES PATENT AND TRADEMARK OFFICE
CERTIFICATE OF CORRECTION

PATENT NO. : 4,221,791

DATED : September 9, 1980

INVENTOR(S) : V. V. Young et al

It is certified that error appears in the above-identified patent and that said Letters Patent are hereby corrected as shown below:

Column 6, line 11, "treated" should read -- tested --

Signed and Sealed this

Fourteenth Day of April 1981

[SEAL]

Attest:

RENE D. TEGTMEYER

Attesting Officer     Acting Commissioner of Patents and Trademarks